(12) United States Patent
Dodds et al.

(10) Patent No.: US 7,595,065 B2
(45) Date of Patent: *Sep. 29, 2009

(54) BREATH FRESHENING AND ORAL CLEANSING PRODUCTS WITH SYNERGISTIC COMBINATIONS OF MAGNOLIA BARK EXTRACT AND ESSENTIAL OILS

(75) Inventors: Michael William James Dodds, LaGrange Park, IL (US); Darci C. Biesczat, Griffith, IN (US); James Roy Maxwell, Chicago, IL (US); Michael J. Greenberg, Northbrook, IL (US)

(73) Assignee: Wm. Wrigley Jr. Company, Chicago, IL (US)

( * ) Notice: Subject to any disclaimer, the term of this patent is extended or adjusted under 35 U.S.C. 154(b) by 313 days.

This patent is subject to a terminal disclaimer.

(21) Appl. No.: 11/393,358

(22) Filed: Mar. 29, 2006

(65) Prior Publication Data

US 2006/0275222 A1  Dec. 7, 2006

Related U.S. Application Data

(63) Continuation-in-part of application No. 10/606,671, filed on Jun. 25, 2003, now Pat. No. 7,347,985, and a continuation-in-part of application No. 10/607,574, filed on Jun. 25, 2003, now abandoned.

(60) Provisional application No. 60/319,346, filed on Jun. 25, 2002, provisional application No. 60/319,370, filed on Jun. 28, 2002.

(51) Int. Cl.
*A61Q 11/00* (2006.01)
*A61K 36/00* (2006.01)

(52) U.S. Cl. ............... 424/725; 424/400; 424/439; 424/49; 424/58; 424/435; 426/615

(58) Field of Classification Search .............. 424/725, 424/400, 439, 49, 58, 435; 426/615
See application file for complete search history.

(56) References Cited

U.S. PATENT DOCUMENTS

| | | | |
|---|---|---|---|
| 1,056,212 | A | 3/1913 | Puetzer et al. |
| 3,452,138 | A | 6/1969 | Granatek et al. |
| 4,547,361 | A | 10/1985 | Steltenkamp et al. |
| 4,562,020 | A | 12/1985 | Hijiya et al. |
| 4,568,560 | A | 2/1986 | Schobel |
| 4,820,544 | A | 4/1989 | Barcelon et al. |
| 4,971,806 | A | 11/1990 | Cherukuri et al. |
| 5,149,521 | A | 9/1992 | Hirose et al. |
| 5,487,902 | A | 1/1996 | Andersen et al. |
| 5,651,997 | A | 7/1997 | Makino et al. |
| 5,939,050 | A | 8/1999 | Iyer et al. |
| 5,948,430 | A | 9/1999 | Zerbe et al. |
| 6,177,096 | B1 | 1/2001 | Zerbe et al. |
| 6,248,309 | B1 | 6/2001 | Iyer et al. |
| 6,280,751 | B1 | 8/2001 | Fletcher et al. |
| 6,284,264 | B1 | 9/2001 | Zerbe et al. |
| 6,495,512 | B1 | 12/2002 | White et al. |
| 6,500,406 | B1 | 12/2002 | Rajaiah et al. |
| 6,500,409 | B1 | 12/2002 | Scherl et al. |
| 6,552,024 | B1 | 4/2003 | Chen et al. |
| 6,582,735 | B2 | 6/2003 | Slogniew et al. |
| 6,596,298 | B2 | 7/2003 | Leung et al. |
| 6,656,493 | B2 | 12/2003 | Dzija et al. |
| 6,703,000 | B2 | 3/2004 | Ning et al. |
| 6,719,962 | B2 | 4/2004 | Day et al. |
| 6,723,326 | B1 | 4/2004 | Farmer |
| 6,726,897 | B2 | 4/2004 | Lawlor et al. |
| 6,740,332 | B2 | 5/2004 | Zyck et al. |
| 6,923,981 | B2 | 8/2005 | Leung et al. |
| 7,025,983 | B2 | 4/2006 | Leung et al. |
| 2001/0018043 | A1 | 8/2001 | Henning et al. |
| 2001/0022964 | A1 | 9/2001 | Leung et al. |
| 2002/0131990 | A1 | 9/2002 | Barkalow et al. |
| 2003/0007997 | A1 | 1/2003 | Lawlor |
| 2003/0008062 | A1 | 1/2003 | Day et al. |
| 2003/0049303 | A1 | 3/2003 | Ning et al. |
| 2003/0224090 | A1 | 12/2003 | Pearce et al. |
| 2004/0081713 | A1 | 4/2004 | Maxwell et al. |

(Continued)

FOREIGN PATENT DOCUMENTS

| | | |
|---|---|---|
| CN | 1094895 A | 11/1994 |
| CN | 1096694 A | 12/1994 |
| CN | 1096699 A | 12/1994 |
| CN | 1115212 A | 1/1996 |
| CN | 1127136 A | 7/1996 |

(Continued)

OTHER PUBLICATIONS

Bang K.H. et al., *Archives of Pharmaceutical Research*, vol. 23, pp. 46-49, 2000.
Chang B. et al., *Planta Medica*, vol. 64, pp. 367-369, 1998.
Ho, K et al., *Phytotherapy Research*, vol. 15, pp. 139-141, 2001.
Kubo I. et al., *J. Agric. Food Chem.*, vol. 41, pp. 2447-2450, 1993.
Mori M. et al., *Holz als Roh-und Werkstoff*, vol. 55, pp. 275-278, 1997.
Park, J. et al., *European Journal of Pharmacology*, vol. 496, pp. 189-195, 2004.

(Continued)

*Primary Examiner*—Ruth A Davis
(74) *Attorney, Agent, or Firm*—Brinks Hofer Gilson & Lione

(57) ABSTRACT

An oral composition for oral cleansing, breath freshening, and anti-microbial benefits includes an oral cavity delivery agent and an antimicrobial active agent including a synergistic combination of *Magnolia* Bark Extract and an essential oil. The oral composition includes chewing gums, candies, and an edible films. Specific antimicrobial active ingredient combinations include *Magnolia* Bark Extract and cinnamon oil or cinnamaldehyde, *Magnolia* Bark Extract and clove bud oil, *Magnolia* Bark Extract and peppermint oil.

27 Claims, No Drawings

U.S. PATENT DOCUMENTS

| | | |
|---|---|---|
| 2004/0086546 A1 | 5/2004 | Maxwell et al. |
| 2004/0253189 A1 | 12/2004 | Maxwell et al. |
| 2004/0253190 A1 | 12/2004 | Maxwell et al. |
| 2004/0253191 A1 | 12/2004 | Maxwell et al. |
| 2004/0253192 A1 | 12/2004 | Maxwell et al. |
| 2004/0253278 A1 | 12/2004 | Maxwell et al. |
| 2004/0258733 A1 | 12/2004 | Maxwell et al. |
| 2005/0008690 A1 | 1/2005 | Miller |
| 2005/0013902 A1 | 1/2005 | Pearce |

FOREIGN PATENT DOCUMENTS

| | | |
|---|---|---|
| CN | 1141194 A | 1/1997 |
| CN | 1073410 C | 10/2001 |
| GB | 1311060 | 3/1973 |
| JP | 57085319 A | 5/1982 |
| JP | SHO-84-175422 | 10/1984 |
| JP | 1151512 | 6/1989 |
| KR | 1996-0007923 | 6/1996 |
| KR | 2002-0003413 | 1/2002 |
| WO | WO 93/15116 | 8/1993 |
| WO | WO 97/35599 | 10/1997 |
| WO | WO 99/18940 | 4/1999 |
| WO | WO 99/51093 | 10/1999 |
| WO | WO 00/42992 A2 | 7/2000 |
| WO | WO 01/82922 | 11/2001 |
| WO | WO 01/85116 A2 | 11/2001 |
| WO | WO 02/43657 A2 | 6/2002 |
| WO | WO 02/091848 A1 | 11/2002 |
| WO | WO 2004/000235 A2 | 12/2003 |
| WO | WO 2004/000235 A3 | 12/2003 |
| WO | WO 2007/011504 | 1/2007 |
| WO | WO 2007/064505 | 6/2007 |

OTHER PUBLICATIONS

Rickard A.H. et al., *Trends in Microbiology*, vol. 11, pp. 94-100, 2003.
Schreiner H.C. et al., *PNAS*, vol. 100, pp. 7295-7300, 2003.
Sharma A. et al., *Oral Microbiology and Immunology*, vol. 20, pp. 39-42, 2005.
Watanabe K. et al. *Japanese Journal of Pharmacology*, vol. 25, pp. 605-607, 1975.
PCT International Search Report, PCT/US2006/025042, Sep. 10, 2006.
PCT Written Opinion, PCT/US2006/025042, Sep. 10, 2006.
PCT International Search Report, PCT/US2007/006989, Dec. 19, 2007.
PCT Written Opinion, PCT/US2007/006989, Dec. 19, 2007.
International Search Report, PCT/US2006/044934, Mar. 14, 2007.
PCT International Search Report, PCT/US2006/044810, Mar. 7, 2007.
PCT Written Opinion, PCT/US2006/044810, Mar. 7, 2007.
PCT International Search Report, PCT/US2006/044933, Mar. 8, 2007.
PCT Written Opinion, PCT/US2006/044933, Mar. 8, 2007.
Al/Zuhair et al., *Pharmacological Studies of Cardamon Oil in Animals. Pharmacological Research*, vol. 34, No. 1/2, 1996.

BREATH FRESHENING AND ORAL CLEANSING PRODUCTS WITH SYNERGISTIC COMBINATIONS OF MAGNOLIA BARK EXTRACT AND ESSENTIAL OILS

RELATED U.S. APPLICATIONS

This application is a continuation-in-part of U.S. patent application Ser. No. 10/606,671, filed Jun. 25, 2003, now U.S. Pat. No. 7,347,985 incorporated by reference herein, which claims priority to provisional patent application Ser. No. 60/319,346, filed Jun. 25, 2002, and of U.S. patent application Ser. No. 10/607,574, filed Jun. 25, 2003, now abandoned, which claims priority to provisional patent application Ser. No. 60/319,370, filed Jun. 28, 2002.

TECHNICAL FIELD

The present invention relates, in general, to oral compositions for breath freshening and, more particularly, to oral compositions containing synergistic combinations of *Magnolia* Bark Extract and essential oils, including cinnamon oil or cinnamaldehyde and clove bud oil, and to synergistic combinations of *Magnolia* Bark Extract and these essential oils.

BACKGROUND

There is considerable consumer demand for products that freshen breath and kill bacteria in the mouth. An oral product with breath freshening and bactericidal benefits is a convenient delivery for oral cleansing in the oral cavity and freshening breath.

Of course, breath freshening is a very important part of everyday life. In order to facilitate proper oral hygiene, oral cleansing and breath freshening practices should be conducted repeatedly throughout the day.

However, oral cleansing and breath freshening may be difficult or inconvenient at times, depending on the nature of the breath freshening desired and the situation in which the breath freshening must occur. Brushing, flossing, cleaning your tongue and gargling using a variety of devices and compositions are common oral care practices well-suited for the privacy of one's home. But, such devices and compositions are less convenient to use away from the home where bathroom facilities might be scarce, unavailable or unsanitary.

SUMMARY

The present invention relates to methods of freshening breath and oral cleansing. Furthermore, the present invention relates to the composition of, and methods of producing an oral product. Specifically, the present invention relates to oral products intended for bactericidal and breath freshening properties. More specifically, the present invention relates to a dentifrice, chewing gum, confection, lozenge, mouthwash, mouth spray, foam or edible film containing a combination of *Magnolia* Bark Extract and essential oils which produce a synergistic effect of bactericidal properties for oral cleansing and breath freshening. The inventive composition effectively inactivates or kills oral bacteria and freshens breath through the consumption of the dentifrice, chewing gum, confection, lozenge, mouthwash, mouth spray, foam or edible film product.

In an aspect of the present invention, the oral composition is chewing gum or any variation including but not limited to bubble gums, pellets, gum balls or sticks. Chewing gums may be coated or not coated and be of a variety of flavors, shapes and sizes. In another aspect of the invention, the oral composition is a confectionery composition including but not limited to hard candy, chewing candy, filled candy and pressed tablets. In yet another aspect of the present invention, the oral composition is an edible film composition, which can be a pullulan-free edible film.

An oral composition for freshening the breath of consumers of the oral composition in accordance with one aspect of the invention includes an oral cavity delivery agent and an antimicrobial active agent including a synergistic combination of *Magnolia* Bark Extract and an essential oil.

An oral composition for freshening the breath of consumers in accordance with another aspect of the invention includes a chewing gum composition including a water soluble bulk portion, at least one flavoring agent, and a gum base portion. The composition also includes an effective amount of an antimicrobial active agent that includes a synergistic combination of *Magnolia* Bark Extract and an essential oil.

In accordance with yet another aspect of the invention, a confectionary composition for freshening the breath of consumers includes at least one of a sugar or a sugar alcohol and an effective amount of an antimicrobial active agent including a synergistic combination of *Magnolia* Bark Extract and an essential oil.

DETAILED DESCRIPTION

It is known to use chewing gum, confections, thin films, and the like as a vehicle for delivering components to the oral cavity which provide oral benefits such as breath freshening and bactericidal properties. Such systems have the advantage of providing a consumer with a convenient and inexpensive method for maintaining oral health and fresh breath throughout the course of the day.

The present invention incorporates a synergistic combination of *Magnolia* Bark Extract and an essential oil as the active component for breath freshening and oral bactericidal benefits. *Magnolia* Bark Extract is known to have bactericidal and anti-fungal properties. Magnolol and honokiol are two components in *Magnolia* Bark Extract with anti microbial activity. The inventors have surprisingly discovered that combinations of *Magnolia* Bark Extract with certain essential oils provide a synergistic combination that reduces bacterial levels below that obtained with either *Magnolia* Bark Extract or the essential oil alone.

In one aspect, the invention comprises a treatment method for reducing the number or activity of bacteria in the oral cavity comprising the steps of providing an oral composition comprising a synergistic combination of *Magnolia* Bark Extract and cinnamon oil or cinnamic aldehyde in an amount sufficient to kill or deactivate oral bacteria and causing a person in need of the treatment to consume the oral composition whereby the bacteria in the oral cavity of the person is reduced or inactivated by the treatment.

In another aspect, the invention comprises a treatment method for reducing the number or activity of bacteria in the oral cavity comprising the steps of providing an oral composition comprising a synergistic combination of *Magnolia* Bark Extract and clove bud oil in an amount sufficient to kill or deactivate oral bacteria and causing a person in need of the treatment to consume the oral composition whereby the bacteria in the oral cavity of the person is reduced or inactivated by the treatment.

In yet another aspect, the invention comprises a treatment method for reducing the number or activity of bacteria in the oral cavity comprising the steps of providing an oral composition comprising a synergistic combination of *Magnolia* Bark Extract and peppermint oil in an amount sufficient to kill or deactivate oral bacteria and causing a person in need of the treatment to consume the oral composition whereby the bacteria in the oral cavity of the person is reduced or inactivated by the treatment.

The oral composition can include additional breath freshening or oral health ingredients, which can also be antimicrobial agents. The additional breath freshening or oral health ingredients can be food acceptable salts of zinc or copper or cooling agents. The additional breath freshening or oral health ingredients can also be a pyrophosphate or polyphosphate.

In one form of the invention, the oral composition is formulated to deliver at least 0.005% concentration of a synergistic combination of *Magnolia* Bark Extract and an essential oil to the oral cavity. In accordance with another form, the oral composition is formulated to deliver at least about 0.01% concentration of a synergistic combination of *Magnolia* Bark Extract and an essential oil to the oral cavity, and in accordance with yet another form of the invention, the oral composition is formulated to deliver at least about 0.1% concentration of *Magnolia* Bark Extract and an essential oil to the oral cavity.

It is also known that *Magnolia* Bark Extract is effective against *Actinobacillus actinomyecetemcomitans, Porphyromonas gingivalis, Prevotella intermedia, Micrococcus luteus,* and *Bacillus subtilis, Prevotella gingivalis, Veillonella disper, Capnocytophaga gingivalis,* periodontic microorganisms and gingival fibroblasts.

Chewing Gum

In accordance with one aspect of the invention, a chewing gum formulation is provided with an effective amount of an active ingredient combination in a chewing gum formulation that includes a synergistic combination of *Magnolia* Bark Extract and an essential oil. In an embodiment of the present invention, the active ingredient combination is a synergistic combination of *Magnolia* Bark Extract and cinnamaldehyde. In another embodiment, the active ingredient combination is a synergistic combination of *Magnolia* Bark Extract and clove bud oil. The active ingredient combination is preferable present in the chewing gum formulation in amounts ranging from about 0.25% up to about 5% by weight of the chewing gum formulation.

In general, a chewing gum composition typically comprises a water-soluble bulk portion, a water-insoluble chewable gum base portion and typically water-soluble flavoring agents. The water-soluble bulk portion dissipates with a portion of the flavoring agent over a period of time during chewing. The gum base portion is retained in the mouth throughout the chew.

The insoluble gum base generally comprises elastomers, resins, fats and oils, softeners and inorganic fillers. The gum base may or may not include wax. The insoluble gum base can constitute approximately 5% to about 95% by weight of the chewing gum, more commonly the gum base comprises 10% to about 50% of the gum, and in some preferred embodiments approximately 25% to about 35% by weight, of the chewing gum.

In a particular embodiment, the chewing gum base of the present invention contains about 20% to about 60% by weight synthetic elastomer, up to about 30% by weight natural elastomer, about 5% to about 55% by weight elastomer plasticizer, about 4% to about 35% by weight filler, about 5% to about 35% by weight softener, and optional minor amounts (about 1% or less by weight) of miscellaneous ingredients such as colorants, antioxidants, etc.

Synthetic elastomers may include, but are not limited to, polyisobutylene with GPC weight average molecular weight of about 10,000 to about 95,000, isobutylene-isoprene copolymer (butyl elastomer), styrenecopolymers having styrene-butadiene ratios of about 1:3 to about 3:1, polyvinyl acetate having GPC weight average molecular weight of about 2,000 to about 90,000, polyisoprene, polyethylene, vinyl acetate vinyl laurate copolymer having vinyl laurate content of about 5% to about 50% by weight of the copolymer, and combinations thereof.

Preferred ranges for polyisobutylene are 50,000 to 80,000 GPC weight average molecular weight; for styrene are 1:1 to 1:3 bound styrene; for polyvinyl acetate are 10,000 to 65,000 GPC weight average molecular weight with the higher molecular weight polyvinyl acetates typically used in bubble gum base; and for vinyl acetate laurate, a vinyl laurate content of 10.

Natural elastomers may include natural rubber, such as smoked or liquid latex and guayule, as well as natural gums, such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva and massaranduba balata.

Elastomer plasticizers may include, but are not limited to, natural rosin esters such as glycerol esters or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha beta and/or any suitable combinations of the foregoing. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium oxide, mono-, di- and tri-phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithin, mono and triglycerides, acetylated monoglycerides, fatty acids (for example, stearic, palmitic, oleic and linoleic acids), and combinations thereof.

Colorants and whiteners may include FD&C dyes and lakes, fruit and vegetable Extracts, titanium dioxide, and combinations thereof.

The base may or may not include wax. An example of a wax-free gum base is disclosed in U.S. Pat. No. 5,286,500, the disclosure of which is incorporated herein by reference.

In addition to a water insoluble gum base portion, a typical chewing gum composition includes a water soluble bulk portion and one or more flavoring agents. The water soluble portion can include bulk sweeteners, high intensity sweeteners, flavoring agents, softeners, emulsifiers, colors, acidulants, fillers, antioxidants, and other components that provide desired attributes.

Softeners are added to the chewing gum in order to optimize the chewability and mouthfeel of the gum. The softeners, which are also known as plasticizers and plasticizing agents, generally constitute between approximately 0.5% to about 15% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners, or bulking agents, include both sugar and sugarless components. Bulk sweeteners typically constitute about 5% to about 95% by weight of the chewing gum, more typically, about 20% to about 80% by weight, and more commonly, about 30% to about 60% by weight of the gum. Sugar sweeteners generally include saccharide components commonly known in the chewing gum art, including but not limited to, sucrose, dextrose, maltose, dextrin, dried invert sugar, fructose, levulose, galactose, corn syrup solids, and the like, alone or in combination. Sugarless sweeteners include, but are not limited to, sugar alcohols such as sorbitol, mannitol, xylitol, hydrogenated starch hydrolysates, maltitol, and the like, alone or in combination.

High intensity artificial sweeteners can also be used, alone or in combination, with the above. Preferred sweeteners include, but are not limited to, sucralose, aspartame, neopentyl-NAPM derivatives such as neotame, salts of acesulfame, altitame, saccharin and its salts, cyclamic acid and its salts, glycyrrhizinate, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Combinations of sugar and/or sugarless sweeteners may be used in chewing gum. Additionally, the softener may also provide additional sweetness such as with aqueous sugar or alditol solutions.

If a low calorie gum is desired, a low caloric bulking agent can be used. Examples of low caloric bulking agents include: polydextrose; raftilose, raftilin; fructooligosaccharides (NutraFlora); Palatinose oligosaccharide; guar gum hydrolysate (Sun Fiber); or indigestible dextrin (Fibersol). However, other low calorie bulking agents can be used.

A variety of flavoring agents can also be used, if desired. The flavor can be used in amounts of about 0.1 to about 15 weight percent of the gum, and preferably, about 0.2% to about 5% by weight. Flavoring agents may include, synthetic flavors or mixtures thereof including, but not limited to, oils derived from plants and fruits such as citrus oils, fruit essences, and the like. In addition to the synergistic active ingredient combination with *Magnolia* Bark Extract of the invention, additional essential oils can also be included a flavoring agents. These oils include peppermint oil, spearmint oil, other mint oils, oil of wintergreen, anise, and the like.

Artificial flavoring agents and components may also be used. Natural and artificial flavoring agents may be combined in any sensorially acceptable fashion. Flavoring may include a cooling agent to enhance the flavor and perceived breath freshening of the product. Cooling agents include menthol, ethyl p-menthane carboxamide, N,2,3-trimethyl-2-isopropyl-butanamide, menthyl glutarate (Flavor Extract Manufacturing Association (FEMA) 4006), menthyl succinate, menthol PG carbonate, menthol EG carbonate, menthyl lactate, menthone glyceryl ketal, menthol glyceryl ether, N-tertbutyl-p-menthane-3-carboxamide, p-menthane-3-carboxylic acid glycerol ester, methyl-2-isopryl-bicyclo (2.2.1), heptane-2-carboxamide, menthol methyl ether and combinations thereof.

Further, additional active ingredients or medicaments may be added for various purposes. If the medicament or active ingredient is water soluble in the chewing gum, it preferably will include a base/emulsifier system which leads to the desired concentration of the medicament in the saliva (more hydrophilic balance). If the medicament or active ingredient is water insoluble, the chewing gum preferably includes a base/emulsifier system which leads to the desired concentration of the medicament in the saliva (more lipophilic balance).

In manufacturing the chewing gum including the active agent or ingredient, the active agent or medicament is added, preferably, early on in the mix. The smaller the amount of active ingredient used, the more necessary it becomes to preblend that particular ingredient to assume uniform distribution throughout the batch of gum. Whether a preblend is used or not, the active agent or medicament should be added within the first five minutes of mixing. For faster release, the active agent may be added late in the process.

Optionally, the chewing gum of the present invention may include additional breath freshening, anti microbial or oral health ingredients, such as food acceptable metallic salts selected from zinc and copper salts of gluconic acid, zinc and copper salts of lactic acid, zinc and copper salts of acetic acid, zinc and copper salts of citric acid, copper chlorophyll, and combinations thereof.

Anti-microbial essential oils and flavor components such as peppermint, methyl salicylate, thymol, eucalyptol, cinnamic aldehyde, eugenol, menthol and combinations thereof may be added to the gum composition.

Dental health ingredients such as fluoride salts, phosphate salts, proteolytic enzymes, lipids, anti-microbials, calcium, electrolytes, protein additives, dental abrasives and combinations thereof may also be added to the gum composition.

In general, chewing gum is manufactured by sequentially adding the various chewing gum ingredients to a commercially available mixer known in the art. After the ingredients have been thoroughly mixed, the gum mass is discharged from the mixer and shaped into the desired form such as rolling sheets and cutting into sticks, extruding into chunks or casting into pellets, which are then coated or panned.

Generally, the ingredients are mixed by first melting the gum base and adding it to the running mixer. The base may also be melted in the mixer itself. Color or emulsifiers may also be added at this time. A softener such as glycerin may also be added at this time, along with syrup and a portion of the bulking agent. Further parts of the bulking agent are added to the mixer. Flavoring agents are typically added with the final portion of the bulking agent. Other optional ingredients are added to the batch in a typical fashion, well known to those of ordinary skill in the art.

The entire mixing procedure typically takes from five to fifteen minutes, but longer mixing times may sometimes be required. Those skilled in the art will recognize that many variations of the above described procedure may be followed.

Chewing gum base and chewing gum product have been manufactured conventionally using separate mixers, different mixing technologies and, often, at different factories. One reason for this is that the optimum conditions for manufacturing gum base, and for manufacturing chewing gum from gum base and other ingredients such as sweeteners and flavors, are so different that it has been impractical to integrate both tasks. Chewing gum base manufacturing involves the dispersive (often high shear) mixing of difficult-to-blend ingredients, such as elastomer, filler, elastomer plasticizer, base softeners/emulsifiers, and sometimes waxes. This process typically requires long mixing times. Chewing gum product manufacture also involves combining the gum base with more delicate ingredients such as product softeners, bulk sweeteners, high intensity sweeteners and flavoring agents using distributive (generally lower shear) mixing, for shorter periods.

Chewing gums of the present invention may also be coated. Pellet or ball gum is prepared as conventional chewing gum, but formed into pellets that are pillow shaped, or into balls. The pellets/balls can be then sugar coated or panned by conventional panning techniques to make a unique sugar coated pellet gum.

Conventional panning procedures generally coat with sucrose, but recent advances in panning have allowed the use of other carbohydrate materials to be used in the place of sucrose. Some of these components include, but are not limited to, dextrose, maltose, palatinose, xylitol, lactitol, hydrogenated isomaltulose and other new alditols or a combination thereof. These materials may be blended with panning modifiers including, but not limited to, gum arabic, maltodextrins, corn syrup, gelatin, cellulose type materials like carboxymethyl cellulose or hydroxymethyl cellulose, starch and modified starches, vegetable gums like alginates, locust bean gum, guar gum, and gum tragacanth, insoluble carbonates like calcium carbonate or magnesium carbonate and talc. Antitack agents may also be added as panning modifiers which allow the use of a variety of carbohydrates and sugar alcohols to be used in the development of new panned or coated gum products. Essential oils may also be added with the sugar coating with *Magnolia* Bark Extract to yield unique product characteristics.

In an embodiment, synergistic combination of *Magnolia* Bark Extract and peppermint oil can be easily added to a hot sugar solution prepared for sugar panning. In another embodiment, *Magnolia* Bark Extract can also be added as a powder blended with a powdered cinnamon oil often used in some types of conventional panning procedures.

Edible Films

In accordance with another aspect of the invention, an edible film formulation is provided with an effective amount of an active ingredient combination in that includes a synergistic combination of *Magnolia* Bark Extract and an essential oil. In an embodiment of the present invention, the active ingredient combination is a synergistic combination of *Magnolia* Bark Extract and cinnamaldehyde. In another embodiment, the active ingredient combination is a synergistic combination of *Magnolia* Bark Extract and clove bud oil. The active ingredient combination is preferable present in the edible film formulation in amounts ranging from about 1.75% up to about 18% by weight of the edible film formulation.

The edible film formulations can include at least three types of film forming agents other than pullulan. Applicants have uniquely discovered that the use of a mixture of at least three types of film forming agents, such as maltodextrins, fillers (for example, microcrystalline cellulose (MCC)) and hydrocolloids (for example, sodium aliginate), can be effectively utilized to prepare stand alone edible films. The edible films are composed of ingredients that are readily available, can be prepared at lower costs and display similar properties as compared to edible films composed of pullulan. In this regard, the edible films can provide a physiologically acceptable film, which is suitably adapted to adhere to oral surfaces of an oral cavity and rapidly dissolve therein.

The edible films can be utilized to deliver or release oral care agent(s). Such agents include anti-microbial agents and salivary stimulants to treat, for example, halitosis, dental plaque, gingivitis, xerostomia, dry mouth, like oral conditions or combinations thereof. Further, the oral care edible film can act as a breath freshener effective against malodor.

The oral cleansing and breath freshening effects of the edible film can be achieved by entrapping the oral care agents within the oral cavity to provide extended efficacy. In this regard, the highly dissolvable edible film can act as a medium through which a pharmaceutically active oral agent can be administered via a mucous membrane of the oral cavity.

Further, the edible films can include a variety of other suitable ingredients, such as softeners, colorants, flavoring agents, emulsifiers, surfactants, thickening agents, binding agents, sweeteners, fragrances, other like ingredients or combinations thereof.

The edible films preferably include a mixture of at least three types of film forming agents, such as maltodextrins, fillers and hydrocolloids. It should be appreciated that the edible film of the present invention can be composed of one or more different compounds associated with each of the at least three types of film forming agents.

The maltodextrin component constitutes between about 5% to about 60% by dry weight of the edible film, preferably about 20% to about 40% by dry weight. The maltodextrin component can be processed in any suitable way.

The hydrocolloid can provide thickness and decrease brittleness of the edible films. The hydrocolloid can include any suitable type, amount and number of hydrocolloids. The hydrocolloid can constitute between about 10% to about 50% by dry weight of the edible film, preferably about 20% to about 30% by dry weight. The hydrocolloid can be derived from, for example, natural seaweeds, natural seed gum, natural plant exudates, natural fiber Extracts, biosynthetic gums, gelatins, biosynthetic process starch or cellulosic materials, alginates, sodium alginate, calcium alginate, carrageenans, guar gum, locust gum, tara gum, gum arabic, ghatti gum, agar gum, xanthan gum, pectin, other like hydrocolloid source material or combinations thereof.

Any suitable food-grade bulk filler can also be added to the edible film. This can reduce any slimy texture as well as provide structure to the film thereby making it more palatable. The filler can constitute about 5% to about 30% by dry weight of the film, preferably about 15% to about 25% by dry weight. The filler can include, for example, microcrystalline cellulose, cellulose polymers, such as wood, magnesium and calcium carbonate, ground limestone, silicates, such as magnesium and aluminum silicate, clay, talc, titanium dioxide, mono-calcium phosphate, di-calcium phosphate, tri-calcium phosphate, other like bulk fillers or combinations thereof.

It is believed that the unique mixture of at least three film forming agents other than pullulan, for example, a maltodextrin, a hydrocolloid and a bulk filler, can provide a stand alone edible film composition which exhibits many of the same desirable properties exhibited by more expensive pullulan-based edible film. Applicants have desirably discovered that the pullulan-free edible film formulation of the present invention can exhibit, for example, clean mouth feel, clean favor and ease of manufacture similar to currently available pullulan-based films.

As previously discussed, a variety of other suitable ingredients can be added to the edible film of the present invention. For example, any suitable medicament for oral cleansing, breath freshening or the like can be added to the film formulation. The medicaments can include, for example, a pH control agent, such as urea and buffers, inorganic components for tartar or caries control, such as phosphates and fluorides, a breath freshening agent such as zinc gluconate, an anti-plaque/anti-gingivitis agent, such as chlorhexidene, CPC, and triclosan, a saliva stimulating agent including, for example, food acids such as citric, lactic, maleic, succinic, ascorbic, adipic, fumaric and tartaric acids, a pharmaceutical agent, a nutraceutical agent, a vitamin, a mineral, other like medicaments or combinations thereof.

The medicaments can be delivered or released into the oral cavity for effective oral treatment, such as oral cleansing and/or breath freshening. In this regard, the film forming agent of the edible film can act to entrap the medicaments within the oral cavity thereby providing extended efficacy thereof. In doing so, it is believed that the pullulan free edible film compositions of the present invention more uniformly release the medicament into the oral cavity for absorption via open wounds or mucous membrane in a greater manner than could be previously achieved. Moreover, it is also believed that the mixture of film forming agents of the present invention can entrap the medicament within the oral cavity for an extended period of time to prolong and enhance the effects of the medicament. In addition, by extending the contact time of the medicament within the oral cavity, the medicament is absorbed to a greater extent thereby increasing its bioavailability.

If reduced levels of film forming agents are utilized, softeners can be used to reduce the brittleness of the resulting films. The softeners, which are also known as plasticizers or plasticizing agents, generally constitute between about up to 20% by dry weight of the film, preferably about 2% to about 10% by dry weight. The softeners can include plasticizers containing, for example, sorbitol and other polyols, glycerin, polyethylene glycol, propylene glycol, hydrogenated starch hydrolysates, corn syrups, other like material or combinations thereof.

The edible film formulations can also include colorants or coloring agents which can be used in any suitable amount to produce the desired color. Coloring agents can include, for example, natural food colors and dyes suitable for food, drug and cosmetic applications. The colorants are typically knows as FD&C dyes and lakes.

A variety of flavoring agents can also be added to the edible films. Any suitable amount and type of artificial and/or natural flavoring agents can be used in any sensorially acceptable fashion. For example, the flavor can constitute about 0.1% to about 20% by dry weight of the film, preferably about 10% to 15%. In addition to the synergistic active ingredient combination with *Magnolia* Bark Extract of the invention, additional essential oils can also be included a flavoring agents. The flavoring agent can include, for example, such as citrus oils, fruit essences, peppermint oil, spearmint oil, other mint oils, clove oils, oil of wintergreen, anise and the like, flavor oils with germ killing properties such as menthol, eucalyptol, thymol, and similar flavoring agents or combinations thereof. The flavoring agents can also include synthetic flavors or mixtures including but not limited to oils delivered from plants and fruits.

The flavor can be enhanced and evenly distributed throughout the product by emulsification. Any suitable amount and type of natural and/or synthetic food-grade emulsifier can be used. For example, the emulsifier can include lecithin, food-grade non-ionic emulsifiers, such as fatty acids ($C_{10}$-$C_{18}$), mono and diacyl glycerides, ox bile Extract, polyglycerol esters, polyethylene sorbitan esters, propolyene glycol, sorbitan monopalmitate, sorbitan monosterate, sorbitan tristearate, enzyme modified lecithin, hyroxylated lecithins, other like emulsifiers or combinations thereof.

The flavors can be emulsified by any suitable emulsification process, such as mechanical processing, vigorous stirring, intense pressure fluctuations that occur in turbulent flow such as homogenization, sonication, colloid milling and the like.

The present invention provides methods of producing the edible film formulations. In general, the edible film formulations are prepared by forming a base solution that includes at least three types of film forming agents, such as maltodextrins, hydrocolloids and fillers and processing the base solution to form an edible film. Typically, the base solution is prepared by adding an initial mixture of dry ingredients to water that is stirred.

To the base solution, additional ingredients, such as flavor/emulsifier blends, sweeteners, softeners, color, the like or combinations thereof, can be added. In an embodiment, the solution is stirred continuously and heated at a temperature ranging from about 40° C. to about 60° C. The solution then can be dried in any suitable manner, thereby, forming the edible film.

It should be appreciated that any suitable type, number and arrangement of process procedures or steps (for example, mixing, heating, drying, cooling, addition of ingredients), process parameters (for example, temperature, pressure, pH, process times) or the like can be utilized.

Confectionary Formulations

In accordance with yet another aspect of the invention, a confectionary formulation is provided with an effective amount of an active ingredient combination in a confectionary formulation that includes a synergistic combination of *Magnolia* Bark Extract and an essential oil. In an embodiment of the present invention, the active ingredient combination is a synergistic combination of *Magnolia* Bark Extract and cinnamaldehyde. In another embodiment, the active ingredient combination is a synergistic combination of *Magnolia* Bark Extract and clove bud oil. The active ingredient combination is preferable present in the confectionary formulation in amounts ranging from about 0.25% up to about 5% by weight of the confectionary formulation.

Confectionery products for this invention may be hard candies, chewy candies, coated chewy center candies and tabletted candies. By way of example, the hard candy is primarily comprised of corn syrup and sugar, and derives its name from the fact that it contains only 1.0% and 4% moisture. In appearance, these types of candies are solid, but they are actually supercooled liquids, which are far below their melting points. There are different types of hard candies. Glass types are usually clear or made opaque with dyes; and Grained Types, which are always opaque.

The continuous process for making the deposited glass types with a sugar base are as follows. Corn syrup is spread over a cylinder heated by high pressure steam. Rapid heat exchange causes the water in the syrup to evaporate. The cooked syrup is discharged, colors and flavors are added. The syrup is cooled and deposited onto a stainless steel conveyor. The syrup can be conveyed directly to hoppers which then discharge directly into molds.

The candy is conveyed to batch rollers, which shapes and sizes the batch. The candy enters a former, which shapes the individual pieces into discs, balls, barrels, etc. The present invention can be made into any shape, circles, squares, triangles etc., also into animal shapes or any other novelty molding available. The candy is then cooled, wrapped and packaged.

For grained types of candy, water and sugar are the basic components being mixed with other ingredients, and cooked at high temperatures about 143-155° C., causing the water to turn to steam. The product is transferred to a cooling wheel, where it is collected in about 63 Kg batches, placed in a pulling machine to aerate the product, and the flavor is added.

The candy is transferred to batch rollers where it is shaped and sized. The candy then enters a former, which shapes the individual pieces. The candy is cooled at a relative humidity of 35% and enters a rotating drum where it is coated with a fine sugar. The candy is then conveyed to the graining room for four hours at 32° C. and 60% humidity. The entrapped air and moisture causes the product to grain.

The present embodiment can be of a variety of shapes, flavors and sizes and may contain sugar or may be sugarless.

In addition to the synergistic active ingredient combination with *Magnolia* Bark Extract of the invention, additional essential oils can also be included a flavoring agents. Flavors used in the present embodiment may be peppermint oils, citrus oils, arvensis, fruit flavors, spearmint oils, and the like.

Colors used in the present embodiment are colorants are typically known as FD&C dyes and lakes.

EXAMPLES

*Magnolia* Bark Extract and Cinnamic Aldehyde Individually

The *Magnolia* Bark Extract used in the present invention is obtained from Guang Zhou Masson Pharmaceutical Co., LTD, 172, ShuiYin Road, Guang Zhou, P. R. China. The *Magnolia* Bark Extract is obtained in the form of a powder. The *Magnolia* Bark Extract is dissolved with the flavor and may be warmed to dissolve prior to making the oral product. The cinnamaldehyde used in the present invention is obtained from Northwestern Flavors, Inc. at 120 N. Aurora Street, West Chicago, Ill. 60185, U.S.A.

In vitro tests were conducted with three subgingival plaque bacteria associated with oral malodor to determine the effectiveness of *Magnolia* Bark Extract and cinnamaldehyde, individually. The MIC (Minimum Inhibitory Concentrations) study protocol is as follows. Chlorhexidine was used as a positive control and sterile water was used as a negative control. The active ingredient (*Magnolia* Bark Extract or cinnamaldehyde) was suspended in 10% methanol. Cinnamaldehyde appeared as uniform suspension. Ninetysix (96) well microtiter plates were used for this study. Each well contained $5 \times 10^5$ colony forming units/mil of bacteria, serially diluted agents and bacterial growth medium. All bacterial cultures were incubated at 37° C. and stationary. Bacterial growth was estimated spectrophotometrically at 660 nm, after 48 hours. The MIC for each test bacteria was defined as the minimum concentration of test compound limiting turbidity to an absorbance of less than a predetermined value at 660 nm.

The MBC (Minimum bactericidal concentrations) were determined using the 96-well microtiter plate serial dilutions as described above for MIC studies. Serial dilution of cultures in wells showing no visible growth were performed and 10 microliters of culture were plated in triplicate on blood agar plates. Viable colonies were scored after incubation of the plates for 48 hours at 37° C. For each test bacterium, the number of CFU/ml were determined in the initial inoculum. The MBC was defined as the lowest concentration of a test compound that killed at least 99.9% of the cells present in the initial inoculum.

The results of the studies performed to obtain minimum inhibitory concentration (MIC) and minimum bactericidal concentration (MBC) of *Magnolia* Bark Extract are as follows. Against *S. mutans* a *Magnolia* Bark Extract of 90% had an MIC of 15.62 μg/ml. For *P. gingivalis*, the 90% *Magnolia* Bark Extract had an MIC of had an MIC of 15.6 μg/ml and an MBC of 31.3.91 μg/ml, and the 65% *Magnolia* Bark Extract had an MIC of 7.82 μg/ml. For *F. nucleatum* the 90% *Magnolia* Bark Extract had had an MIC of 15.6 μg/mil and an MBC of 31.3.91 μg/ml and an MBC of 7.82 μg/ml. Against the same organism, the 65% *Magnolia* Bark Extract had an MIC and MBC of 7.82 μg/ml. Chlorhexidine was the positive control and produced an MIC and MBC of 1.25 μg/ml for all three bacteria. The solvent of water with 10% methanol and 3.8% Tween 80 had no noticeable growth inhibitory effects on any of the three bacteria in the study.

The results of the studies performed to obtain minimum inhibitory concentration (MIC) and minimum bactericidal concentration (MBC) of cinnamaldehyde are as follows. Against *S. mutans*, cinnamaldehyde of 90% had an MIC of 15.62 μg/ml. For *P. gingivalis*, the 90% *Magnolia* Bark Extract had an MIC of cinnamaldehyde had an MIC of 15.6 μg/ml and an MBC of 31.3.91 μg/ml. For *F. nucleatum* the 90% *Magnolia* Bark Extract had cinnamaldehyde had an MIC of 15.6 μg/ml and an MBC of 7.82 μg/ml. Against the same organism, the 65% *Magnolia* Bark Extract had an MIC and MBC of 7.82 μg/ml. Chlorhexidine was the positive control and produced an MIC and MBC of 1.25 μg/ml for all three bacteria. The solvent of water with 10% methanol had no noticeable growth inhibitory effects on any of the three bacteria in the study.

Synergistic Combination of *Magnolia* Bark Extract and Cinnamic Aldehyde

Biofilms were grown by incubation of saliva bacteria with saliva-treated hydroxyapatite (HA) discs in sterile 24-well cell culture plates. The media was supplemented with saliva (25% total volume) and the discs were transferred frequently during the growth phases to encourage growth of a dental plaque-like biofilm. The biofilms were allowed to develop for up to 72 hours. On days two and three of the experiment, the biofilms were exposed to the active ingredients three times a day for five minutes. The specific experimental steps are described below.

A mixed culture system that utilizes the bacteria from freshly-collected stimulated whole saliva was used. Saliva cell pellets were used to inoculate saliva-coated hydroxyapatite (S-HA) discs. The discs were placed in 24-well cell culture plates and incubated for up to 3 days. The biofilms were exposed to actives on days 2 and 3 (starting at 18 hours), and quantified on day 4. The bacteria counts were determination using optical density (OD) measurements at 600 nm. Thus, the five experimental stages are: 1) pellicle formation; 2) bacterial attachment; 3) biofilm growth; 4) exposure to actives; and 5) bacterial enumeration. The five experimental stages are described in more detail below.

A. Disc Preparation—Pllicle Formation

HA Discs were ultrasonically washed in deionized water and air-dried, then autoclaved. The discs were placed in a 24-well plate with 1 ml 50% sterile saliva for 2 hours and slowly agitated at room temperature. The plates were then placed on a thermomixer at 350 rpm. The saliva was suctioned and then the discs were transferred to fresh wells for bacterial attachment.

B. Attachment Phase

The discs were placed into 1 ml saliva bacterial suspension (see below) at 300 rpm on the thermomixer and placed in an incubator at 37° C. for 2 hours.

C. Biofilm Formation

The bacterial suspension was removed, and the discs were transferred to fresh wells. One ml of supplemented saliva medium was added and the plate placed in the incubator for overnight incubation and for the duration of the experiment (up to 72 hours).

D. Exposure to Active Ingredients

Each morning on days 2 and 3, actives were prepared at the appropriate concentration in phosphate buffered saline (PBS). The PBS was used as a negative control and full strength Listerine® mouthwash was used as the positive control. In addition to the negative and positive controls, the active ingredients used in the experiment included *Magnolia* Bark Extract alone, cinnamaldehyde alone, and a combination of *Magnolia* Bark Extract and cinnamaldehyde. The active ingredient combination of *Magnolia* Bark Extract and clove bud oil was also tested in the experiment. One ml of active ingredients and controls were placed into fresh wells, and the discs were transferred to these wells for 5 minutes. The Listerine® control exposure was one minute, two times a day to mimic the standard mouth-rinse procedure. The exposure to active ingredients was carried out three times each day, at 8:00 a.m., 12:00 noon, and 4:00 p.m. After the timed exposure, the solution is removed and the discs washed twice with PBS, then transferred to fresh medium. The medium used during the day was Trypticase soy broth, with 0.5% sucrose.

E. Assessment

On day 4 the discs were removed from the medium and placed into tubes with 2.5 ml of PBS, vortexed for 20 seconds, and then placed in an ultrasonic bath for another 20 seconds. The suspension was transferred into cuvettes and the OD measured at 600 nm.

The experimental results for the active ingredients *Magnolia* Bark Extract (MBE) and cinnamaldehyde (CA) are shown below in Table 1.

TABLE 1

MBE and Cinnamic Aldehyde
OD and Percent Reduction vs. Control (PBS)
N = 3 per group

| Active Ingredient | OD at 600 nm | Percent Reduction |
| --- | --- | --- |
| Control (PBS) | 0.286 | — |
| Listerine ® | 0.070 | 76 |
| MBE 1000 ppm | 0.118 | 59 |
| CA 5000 ppm | 0.130 | 54 |
| CA 10000 ppm | 0.119 | 58 |
| MBE 1000 ppm:CA 5000 ppm | 0.082 | 71 |
| MBE 1000 ppm:CA 10000 ppm | 0.074 | 74 |

The percent reduction appearing in Table 1 above for each test sample represents the percentage difference in the measured OD versus the OD for the negative control PBS. The data shown in Table 1 indicates that active ingredient combinations of MBE and CA are more effective at reducing bacteria levels than either MBE or CA alone.

The experimental results for the active ingredients *Magnolia* Bark Extract (MBE) and clove bud oil (CBO) are shown below in Table 2.

TABLE 2

MBE and Clove Bud Oil
OD and Percent Reduction vs. Control (PBS)
N = 3 per group

| Active Ingredient | OD at 600 nm | Percent Reduction |
| --- | --- | --- |
| Control (PBS) | 0.231 | — |
| Listerine ® | 0.044 | 81 |
| MBE 1000 ppm | 0.054 | 77 |

TABLE 2-continued

MBE and Clove Bud Oil
OD and Percent Reduction vs. Control (PBS)
N = 3 per group

| Active Ingredient | OD at 600 nm | Percent Reduction |
| --- | --- | --- |
| CBO 1000 ppm | 0.141 | 39 |
| CBO 50000 ppm | 0.040 | 83 |
| MBE 1000 ppm:CBO 1000 ppm | 0.044 | 81 |
| MBE 1000 ppm:CBO 50000 ppm | 0.032 | 86 |

The percent reduction appearing in Table 2 above for each test sample represents the percentage difference in the measured OD versus the OD for the negative control PBS. The data shown in Table 2 indicates that active ingredient combinations of 1000 ppm MBE and 500 ppm CBO are more effective at reducing bacteria levels than either MBE or CBO alone.

Exemplary Product Formulations

The following are examples of product formulations including synergistic combinations of *Magnolia* Bark Extract and an essential oil (Active Ingredient Combination). The examples are not intended to exclude other variations in formulations and the present invention is not limited to these formulations.

By way of example and not limitation, the following examples illustrate various chewing gum formulations in accordance with an embodiment of the present invention.

TABLE 3

Antimicrobial Gum Formulas
(dry weight percent basis)

| Ingredient | Example 1 | Example 2 | Example 3 | Example 4 | Example 5 |
| --- | --- | --- | --- | --- | --- |
| Gum Base | 26.00 | 26.00 | 26.00 | 27.5 | 27.5 |
| Talc powder | 3.00 | 3.00 | 3.00 | 3.00 | 3.00 |
| NaHCO₃Glycerine | 0.50 | 0.50 | 0.50 | 0.50 | 0.50 |
| Sorbitol | 49.71 | 50.96 | 48.71 | 48.71 | 44.71 |
| Glycerol | 15.01 | 15.01 | 15.01 | 15.01 | 15.01 |
| Mannitol | 1.52 | 1.52 | 1.52 | 1.52 | 1.52 |
| Maltitol | 0.76 | 0.76 | 0.76 | 0.76 | 0.76 |
| Water | 1.18 | 1.18 | 1.18 | 1.18 | 1.18 |
| Aspartame | 0.53 | 0.53 | 0.53 | 0.53 | 0.53 |
| Color | 0.01 | 0.01 | 0.01 | 0.01 | 0.01 |
| Zein | 0.04 | 0.04 | 0.04 | 0.04 | 0.04 |
| NaOH | 0.01 | 0.01 | 0.01 | 0.01 | 0.01 |
| Acesulfame Potassium | 0.13 | 0.13 | 0.13 | 0.13 | 0.13 |
| Active Ingredient Combination | 1.50 | 0.25 | 2.50 | 1.00 | 5.00 |
| Hydroxy-propyl-methylcellulose | 0.10 | 0.10 | 0.10 | 0.10 | 0.10 |
| Total | 100.00 | 100.00 | 100.00 | 100.00 | 100.00 |

TABLE 4

Antimicrobial Gum Formulas
(dry weight percent basis)

| Ingredient | Example 6 | Example 7 | Example 8 | Example 9 | Example 10 |
| --- | --- | --- | --- | --- | --- |
| Gum Base | 19.46 | 20.71 | 19.46 | 19.46 | 18.46 |
| Sugar | 62.13 | 62.13 | 61.13 | 62.63 | 61.63 |
| Corn Syrup | 15.57 | 15.57 | 15.57 | 15.57 | 13.57 |
| Color | 0.67 | 0.67 | 0.67 | 0.67 | 0.67 |

TABLE 4-continued

Antimicrobial Gum Formulas
(dry weight percent basis)

| Ingredient | Example 6 | Example 7 | Example 8 | Example 9 | Example 10 |
|---|---|---|---|---|---|
| P.A. | 0.67 | 0.67 | 0.67 | 0.67 | 0.67 |
| Active Ingredient Combination | 1.50 | 0.25 | 2.50 | 1.00 | 5.00 |
| Total % | 100.00 | 100.00 | 100.00 | 100.00 | 100.00 |

By way of example and not limitation, the following examples illustrate various edible film formulations in accordance with an embodiment of the present invention.

TABLE 5

Antimicrobial Edible Film Formulations
(dry weight percent)

| Ingredient | Example 11 | Example 12 | Example 13 | Example 14 | Example 15 |
|---|---|---|---|---|---|
| Maltodextrin | 25.05 | 47.00 | 31.20 | 36.80 | 21.00 |
| Sodium Alginate | 22.50 | — | 19.00 | — | 12.00 |
| Calcium Alginate | — | 15.15 | — | 11.45 | — |
| Carageenan | — | — | — | — | 12.00 |
| Microcrystalline Cellulose | 20.00 | 25.75 | 9.00 | 18.80 | 13.00 |
| Calcium Carbonate | — | 2.45 | — | — | — |
| Glycerin | 12.25 | 10.00 | 8.00 | — | 9.5 |
| Sorbitol | — | — | — | 6.00 | 1.55 |
| Propylene Glycol | — | — | 3.65 | 5.00 | — |
| Menthol | 1.00 | 0.05 | — | 1.25 | — |
| Eucalyptol | — | 0.05 | — | 1.00 | — |
| Maleic Acid | — | — | — | — | 1.35 |
| Citric Acid | — | — | 1.25 | — | 1.00 |
| Chlorohexidene | 1.85 | — | — | 1.00 | — |
| Triclosan | — | 1.25 | — | 1.00 | — |
| Flavor | 9.40 | 11.00 | 12.00 | 14.00 | 10.00 |
| High Intensity Sweetener | 1.25 | 1.00 | 1.05 | 1.45 | 1.50 |
| Active Ingredient Combination | 1.00 | 3.00 | 5.00 | 8.00 | 10.0 |
| Color | 0.05 | 0.05 | 0.05 | 0.05 | 0.10 |
| Total % | 100.00 | 100.00 | 100.00 | 100.00 | 100.00 |

TABLE 6

Antimicrobial Edible Film Formulations
(dry weight percent basis)

| Ingredient | Example 16 | Example 17 | Example 18 | Example 19 | Example 20 |
|---|---|---|---|---|---|
| Maltodextrin | 35.00 | 32.30 | 28.15 | 32.50 | 30.00 |
| Sodium Alginate | 22.15 | 19.10 | 17.00 | 28.15 | — |
| Carageenan | — | — | — | — | 20.15 |
| Microcrystalline Cellulose | 20.00 | 18.00 | 17.00 | 17.00 | 18.00 |
| Gum Arabic | — | — | 11.00 | — | — |
| Glycerin | 7.30 | 15.00 | 7.30 | 7.30 | 7.30 |
| Flavor | 11.00 | 11.00 | 11.00 | 11.00 | 11.00 |
| Lecithin | 2.00 | 0.05 | 2.00 | 2.00 | 2.00 |
| High Intensity Sweetener | 1.50 | 1.50 | 1.50 | 1.50 | 1.50 |
| Active Ingredient Combination | 1.00 | 3.00 | 5.00 | 0.50 | 10.0 |
| Color | 0.05 | 0.05 | 0.05 | 0.05 | 0.05 |
| Total | 100.00 | 100.00 | 100.00 | 100.00 | 100.00 |

By way of example and not limitation, the following examples illustrate various confectionery formulations in accordance with an embodiment of the present invention.

TABLE 7

Antimicrobial Candy Formulations
(dry weight percent basis)

| Ingredient | Example 21 | Example 22 | Example 23 | Example 24 | Example 25 |
|---|---|---|---|---|---|
| Corn Syrup | 45.00 | 43.00 | — | — | 47.00 |
| Sugar | 53.49 | 50.00 | — | — | 47.00 |
| Polyalcohols | — | — | 95.00 | 94.00 | — |
| Flavor | 1.00 | 5.00 | 3.00 | 2.00 | 2.50 |
| Color | 0.50 | 1.00 | 0.60 | 0.80 | 0.50 |
| Active Ingredient Combination | 0.01 | 1.00 | 1.20 | 3.00 | 3.00 |
| High Intensity Sweetener | — | — | 0.20 | 0.20 | — |
| Total | 100.00 | 100.00 | 100.00 | 100.00 | 100.00 |

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims and equivalents thereof.

The invention claimed is:
1. An oral composition for freshening the breath of consumers, the oral composition comprising:
   (a) an oral cavity delivery agent; and
   (b) an antimicrobial active agent comprising a synergistic combination of *Magnolia* Bark Extract and peppermint oil,
   wherein the synergistic combination comprises a ratio of *Magnolia* Bark Extract and peppermint oil of about 1:1 to about 1:10.
2. An oral composition for freshening the breath of consumers, the oral composition comprising:
   (a) an oral cavity delivery agent; and
   (b) an antimicrobial active agent comprising a synergistic combination of *Magnolia* Bark Extract and cinnamon oil,
   wherein the synergistic combination comprises a ratio of *Magnolia* Bark Extract and cinnamon oil of about 1:5 to about 1:10.

3. An oral composition
for freshening the breath of consumers, the oral composition comprising:
(a) an oral cavity delivery agent; and
(b) an antimicrobial active agent comprising a synergistic combination of *Magnolia* Bark Extract and clove bud oil,
wherein the synergistic combination comprises a ratio of *Magnolia* Bark Extract and clove bud oil of about 1:1 to about 1:5.

4. A chewing gum composition for freshening the breath of consumers, the composition comprising:
(a) a water soluble bulk portion;
(b) at least one flavoring agent;
(c) a gum base portion; and
(d) an effective amount of an antimicrobial active agent comprising a synergistic combination of *Magnolia* Bark Extract and peppermint oil,
wherein the synergistic combination comprises a ratio of *Magnolia* Bark Extract and peppermint oil of about 1:1 to about 1:10.

5. The chewing gum composition of claim 4 wherein the synergistic combination is present in the chewing gum formulation in amounts ranging from about 1.5% up to about 5% by weight of the chewing gum formulation.

6. The chewing gum composition of claim 4 further comprising a coating and wherein the synergistic combination is included in the coating.

7. A chewing gum composition for freshening the breath of consumers, the composition comprising:
(a) a water soluble bulk portion;
(b) at least one flavoring agent;
(c) a gum base portion; and
(d) an effective amount of an antimicrobial active agent comprising a synergistic combination of *Magnolia* Bark Extract and cinnamon oil,
wherein the synergistic combination comprises a ratio of *Magnolia* Bark Extract and cinnamon oil of about 1:5 to about 1:10.

8. The chewing gum composition of claim 7 further comprising a coating and wherein the synergistic combination is included in the coating.

9. The chewing gum composition of claim 7 wherein the synergistic combination is present in the chewing gum formulation in amounts ranging from about 1.5% up to about 5% by weight of the chewing gum formulation.

10. A chewing gum composition for freshening the breath of consumers, the composition comprising:
(a) a water soluble bulk portion;
(b) at least one flavoring agent;
(c) a gum base portion; and
(d) an effective amount of an antimicrobial active agent comprising a synergistic combination of *Magnolia* Bark Extract and clove bud oil,
wherein the synergistic combination comprises a ratio of *Magnolia* Bark Extract and clove bud oil of about 1:1 to about 1:5.

11. The chewing gum composition of claim 10 further comprising a coating and wherein the synergistic combination is included in the coating.

12. The chewing gum composition of claim 10 wherein the synergistic combination is present in the chewing gum formulation in amounts ranging from about 1.5% up to about 5% by weight of the chewing gum formulation.

13. A confectionary composition for freshening the breath of consumers, the composition comprising:
(a) at least one of a sugar or a sugar alcohol; and
(b) an effective amount of an antimicrobial active agent comprising a synergistic combination of *Magnolia* Bark Extract and clove bud oil,
wherein the synergistic combination comprises a ratio of *Magnolia* Bark Extract to clove bud oil of about 1:1 to about 1:10.

14. The confectionary composition of claim 13 wherein the synergistic combination is present in the confectionary formulation in amounts ranging from about 0.1% up to about 3% by weight of the confectionary formulation.

15. The confectionary composition of claim 13 the synergistic combination is present in the confectionary formulation in amounts ranging from about 1.5% up to about 5% by weight of the confectionary formulation.

16. The confectionary composition of claim 13 further comprising a coating and wherein the synergistic combination is included in the coating.

17. A confectionary composition for freshening the breath of consumers, the composition comprising:
(a) at least one of a sugar or a sugar alcohol; and
(b) an effective amount of an antimicrobial active agent comprising a synergistic combination of *Magnolia* Bark Extract and peppermint oil,
wherein the synergistic combination comprises a ratio of *Magnolia* Bark Extract to peppermint oil of about 1:1 to about 1:10.

18. The confectionary composition of claim 17 further comprising a coating and wherein the synergistic combination is included in the coating.

19. The confectionary composition of claim 17 wherein the synergistic combination is present in the confectionary formulation in amounts ranging from about 0.1% up to about 3% by weight of the confectionary formulation.

20. The confectionary composition of claim 17 the synergistic combination is present in the confectionary formulation in amounts ranging from about 1.5% up to about 5% by weight of the confectionary formulation.

21. A confectionary composition
freshening the breath of consumers, the composition comprising:
(a) at least one of a sugar or a sugar alcohol; and
(b) an effective amount of an antimicrobial active agent comprising a synergistic combination of *Magnolia* Bark Extract and cinnamon oil,
wherein the synergistic combination comprises a ratio of *Magnolia* Bark Extract and cinnamon oil of about 1:5 to about 1:10.

22. The confectionary composition of claim 21 further comprising a coating and wherein the synergistic combination is included in the coating.

23. The confectionary composition of claim 21 wherein the synergistic combination is present in the confectionary formulation in amounts ranging from about 0.1% up to about 3% by weight of the confectionary formulation.

24. The confectionary composition of claim 21 the synergistic combination is present in the confectionary formulation in amounts ranging from about 1.5% up to about 5% by weight of the confectionary formulation.

25. An oral composition for freshening the breath of consumers, the oral composition comprising a synergistic combination of *Magnolia* Bark Extract and peppermint oil in a ratio of *Magnolia* Bark Extract to peppermint oil of at least about 1:5.

26. An oral composition for freshening the breath of consumers, the oral composition comprising a synergistic combination of *Magnolia* Bark Extract and cinnamon oil in a ratio of *Magnolia* Bark Extract to cinnamon oil of at least about 1:5.

27. An oral composition for freshening the breath of consumers, the oral composition comprising a synergistic combination of *Magnolia* Bark Extract and clove bud oil in a ratio of *Magnolia* Bark Extract to clove bud oil of at least about 1:5.

* * * * *